US00PP28968P2

(12) United States Plant Patent
Benetka

(10) Patent No.: US PP28,968 P2
(45) Date of Patent: Feb. 20, 2018

(54) ***WEIGELA* PLANT NAMED 'VUKOZ083328'**

(50) Latin Name: *Weigela hybrida*
Varietal Denomination: VUKOZ083328

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,318

(22) Filed: Sep. 2, 2016

(51) Int. Cl.
*A01H 5/02* (2006.01)

(52) U.S. Cl.
USPC ..... Plt./226

(58) Field of Classification Search
None
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZ083328' is disclosed, characterized by deep magenta flowers and abundant flowering. The new variety is a *Weigela*, normally produced as an outdoor garden plant.

3 Drawing Sheets

Latin name of the genus and species: *Weigela hybrida.*
Variety denomination: 'VUKOZ083328'.

BACKGROUND OF THE INVENTION

The new *Weigela* cultivar is a product of a planned breeding program conducted by the inventor, Vojtech Benetka, in Pruhonice, Czech Republic. The objective of the breeding program was to produce new *Weigela* varieties for ornamental garden purposes. The open pollination resulting in this new variety was made in 2008.

The seed parent is a proprietary, unpatented, *Weigela* referred to as '05-34-1'. The pollen parent is unidentified due to open pollination. The new variety was selected as a potentially interesting new plant in 2013, at a research nursery in Pruhonice, Czech Republic.

Asexual reproduction of the new cultivar 'VUKOZ083328' by softwood cuttings was first performed in 2013, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ083328' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZ083328' These characteristics in combination distinguish 'VUKOZ083328' as a new and distinct *Weigela* cultivar:

1. Deep magenta colored flowers.
2. Abundant flowering.

PARENT COMPARISON

Plants of the new cultivar 'VUKOZ083328' are similar to plants of the seed parent in most horticultural characteristics, however, plants of the new cultivar 'VUKOZ083328' differ in the following;

1. New cultivar has magenta flowers, whereas the seed parent has crimson flowers.

COMMERCIAL COMPARISON

Plants of the new cultivar 'VUKOZ083328' can be compared to the patented commercial variety *Weigela* 'Bokrasopea' (U.S. Plant Pat. No. 24,585). These varieties are similar in most horticultural characteristics; however 'VUKOZ083328' differs in the following:

1. New cultivar has deep magenta colored flowers whereas the commercial comparator has more crimson colored flowers.
2. New cultivar has larger flowers than the commercial comparator.

BRIEF DESCRIPTION OF THE PHOTOGRAPHS

Figure 1:
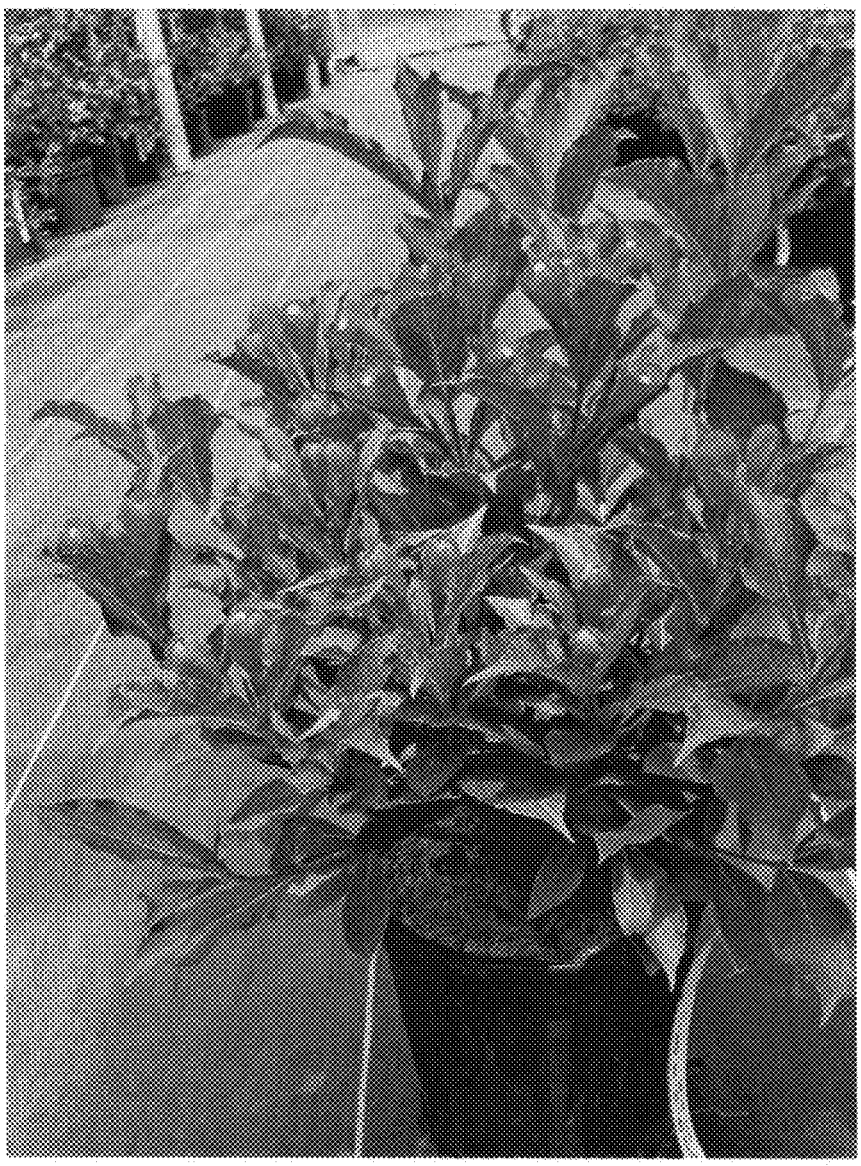

The accompanying photograph in FIG. 1 illustrates in full color a typical plant of 'VUKOZ083328' grown in a 2 gallon container.

Figure 2:
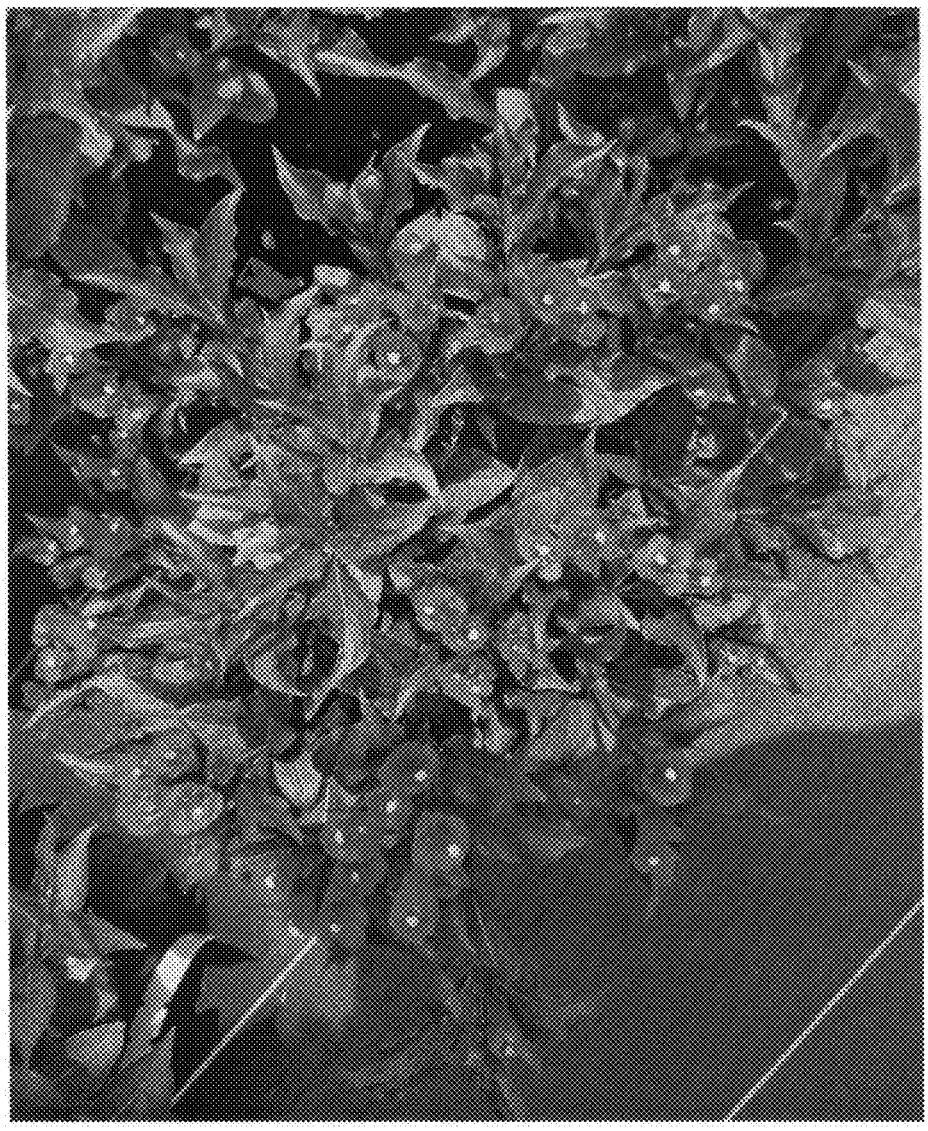

FIG. 2 illustrates a top view of the same plant. Age of the plant photographed is approximately 2 years.

Figure 3:
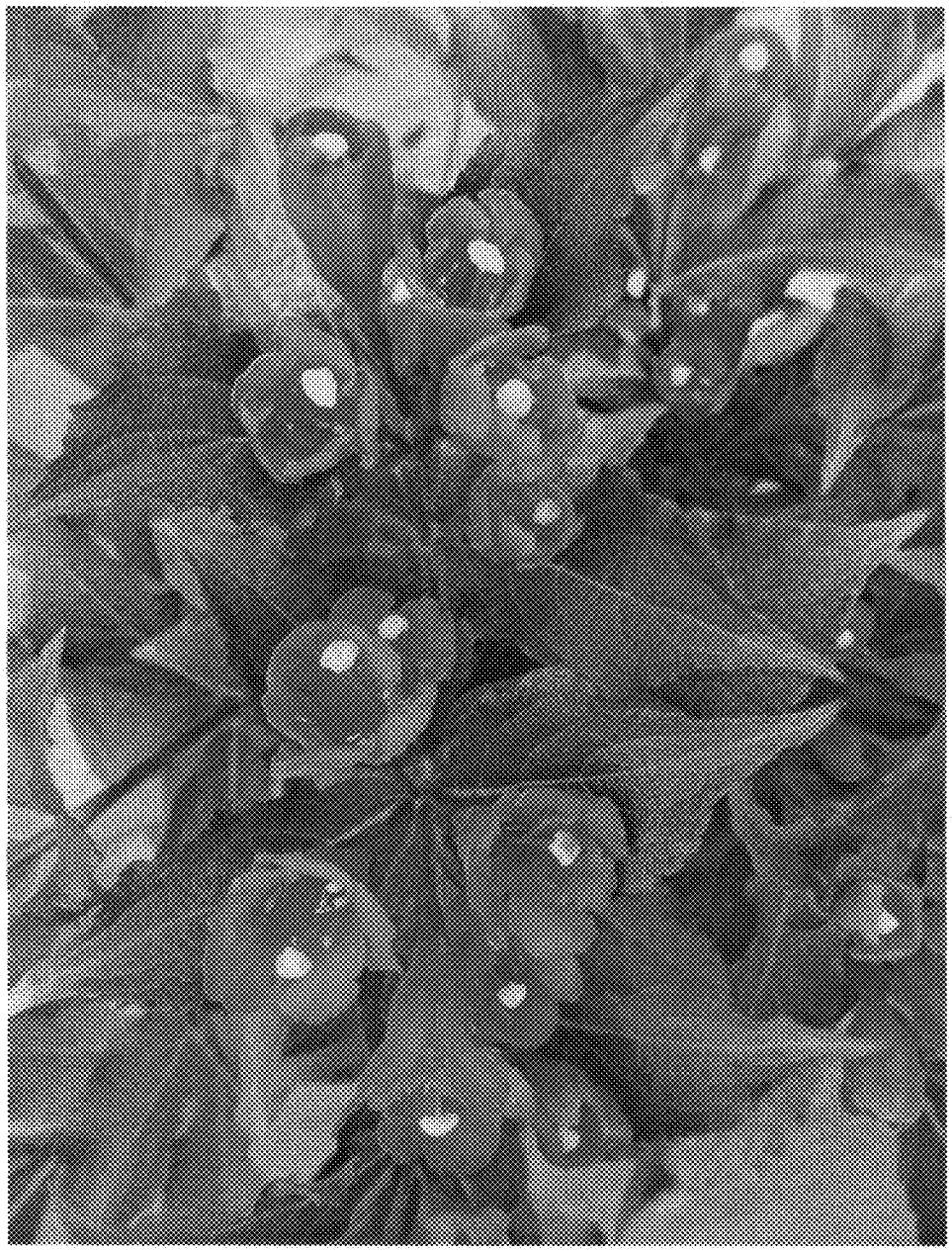

FIG. 3. illustrates a close up view of flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZ083328' plants grown in a polyhouse in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZ083328'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.

Age of plant described: Approximately 2 years old.

Growth habit: Compact growth with good branching.

Pot size of plant described: 2 gallon container.

Overall plant shape: Upright and rounded.

Height: 80 cm.

Plant spread: 85 cm.

Growth rate: Medium.

Plant vigor: Strong.

Branching characteristics: Opposite.

Length of primary lateral branches: 50 cm.

Diameter of lateral branches: 1.0 cm.

Quantity of lateral branches: 38.

Stem:

- *Stem appearance*.—Round.
- *Stem strength*.—Strong.
- *Aspect*.—40° to 45°.
- *Color*.—Near RHS Yellow-Green 145B blended with Brown 200D.
- *Pubescence*.—Yes.

Internode length: Range is 2.5 to 4.5 cm.

FOLIAGE

Leaf:

- *Arrangement*.—Opposite.
- *Leaf shape*.—Ovate-oblanceolate.
- *Average length*.—Approximately 6.5 cm.
- *Average width*.—Approximately 3.0 cm.
- *Apex*.—Acute.
- *Base*.—Acute to cuneate.
- *Margin*.—Serrulate.
- *Texture of top surface*.—Slight pubescence.
- *Texture of bottom surface*.—Pubescent, to a greater extent than upper surface.
- *Color*.—Young foliage upper side: Near RHS Green 137A. Young foliage under side: Near RHS Green 139C. Mature foliage upper side: Near RHS Green 137A. Mature foliage under side: Near RHS Green 139C.
- *Venation*.—Pattern: Pinnate. Color upper side: Near RHS Yellow-Green 153A. Color under side: Near RHS Yellow-Green 145B.
- *Petiole*.—Length: 3.0 mm. Diameter: 1.5 mm. Petiole color upper side: Near RHS Green 145B. Petiole color lower side: Near RHS Green 145C. Petiole Texture: Pubescent.
- *Foliage durability*.—Very durable.

FLOWER

Natural flowering season: Late spring to summer.

Inflorescence type and habit: Umbel to panicle.

Inflorescence height: 9.0 cm.

Inflorescence width: 6.7 cm.

Quantity of flowers per inflorescence: 8 to 10.

Quantity of flowers per plant: 100 to 300 flowers and buds on a mature plant.

Individual flowers:

- *Flower shape*.—Salverform.
- *Flower aspect*.—Upward and slightly outward.
- *Flowering arrangement*.—Single salverform flower, the majority of which are in groups of 2 to 4.
- *Size*.—Diameter: Approximately 2.2 cm. Depth: Approximately 2.5 cm.
- *Flower other characteristics*.—Persistence: Self cleaning. Fragrance: No scent.

Bud:

- *Shape*.—Obovate to spatulate.
- *Length*.—2.6 cm.
- *Diameter*.—8.5 mm.
- *Color*.—Between RHS Red 53B and Red-Purple 60B.

Petal:

- *Petal arrangement*.—Whorled, fused at opening of throat.
- *Number of petals per flower*.—5 to 6.
- *Petal shape*.—Obovate to oblanceolate.
- *Petal base*.—Fused at throat.
- *Margin*.—Entire, slightly undulate.
- *Tip shape*.—Obtuse.
- *Length*.—1.0 cm.
- *Width*.—8.5 cm.
- *Texture*.—Upper: Smooth. Lower: Smooth.
- *Color*.—When opening: Upper side: Near RHS Red-Purple 61B blended, with near RHS Red-Purple 60A. Under side: Near RHS Red-Purple 61B blended, with near RHS Red-Purple 60A with stripes near RHS White 155B. Fully open: Upper side: Near RHS Red-Purple 61B, blended with near RHS Red-Purple 60A. Under side: Near RHS Red-Purple 61B, blended with near RHS Red-Purple 60A. Fades to: Near RHS Red-Purple 61B blended, with near RHS Red-Purple 60A.
- *Flower tube*.—Length: 2.2 cm. Diameter, base: 2.0 mm. Color: Near RHS Red-Purple 61B, blended with near RHS Red-Purple 60A with stripes of near RHS White 155B.
- *Throat*.—Texture: Smooth. Color: Near RHS Red-Purple 61B, blended with near RHS Red-Purple 60A with one spot near RHS Yellow-Orange 18A.

Sepal:

- *Arrangement*.—Unguiculate, fused at base.
- *Appearance*.—Long, narrowly triangular.
- *Number*.—5.
- *Shape*.—Narrowly triangular.
- *Tip*.—Acute.
- *Base*.—Obtuse.
- *Margin*.—Entire.
- *Length*.—8 mm.
- *Width*.—1 mm.
- *Texture, upper*.—Smooth, coriaceous.
- *Texture, lower*.—Smooth, coriaceous.

*Color*.—Upper surface at maturity: Near RHS Yellow-Green 145B blended with near RHS Red-Purple 63A. Under surface at maturity: Near RHS Yellow-Green 145B blended with near RHS Red-Purple 63A.

Peduncle:

*Length*.—7.0 mm.

*Diameter*.—1.0 mm.

*Color*.—Near RHS Yellow-Green 145B blended with near RHS Red-Purple 63A.

*Orientation*.—Upright/outward.

*Strength*.—Good.

*Texture*.—Smooth, coriaceous, slightly pubescent.

Pedicel:

*Length*.—1.5 cm.

*Diameter*.—1.0 mm.

*Angle*.—Upright and outward.

*Strength*.—Good.

*Texture*.—Smooth, coriaceous, slightly pubescent.

*Color*.—Near RHS Yellow-Green 145B blended with near RHS Red-Purple 63A.

REPRODUCTIVE ORGANS

Stamens:

*Number*.—5 to 6.

*Filament length*.—2.5 cm.

*Filament color*.—Near RHS Red-Purple 63B blended with near RHS White 155B.

Anthers:

*Shape*.—Linear, slightly oblong.

*Length*.—5 mm.

*Color*.—Near RHS White 155B which fades to Greyed-Orange 165D with age/development.

*Pollen color*.—Near RHS White 155B.

*Pollen amount*.—Moderate.

Pistil:

*Number*.—1 per flower.

*Length*.—3.1 cm.

*Style*.—Length: 3.3 cm. Color: Near RHS White 155B blended with near RHS Red-Purple 63D.

*Stigma*.—Color: Near RHS Yellow-White 158B. Shape: Globular, flat-bottomed.

OTHER CHARACTERISTICS

Seeds and fruits: Not observed.

Disease/pest resistance: Neither resistance nor susceptibility to normal diseases and pests of *Weigela* have been observed aside from good mildew resistance.

Temperature tolerance: The new variety tolerates temperatures between −31° C. to 38° C.

Environmental stressors: Good resistance to wind and rain.

What is claimed is:

1. A new and distinct cultivar of *Weigela hybrida* plant named 'VUKOZ083328' as herein illustrated and described.

* * * * *